United States Patent [19]

Hayden et al.

[11] 4,168,247

[45] Sep. 18, 1979

[54] CATALYSTS FOR THE PRODUCTION OF ALKYLENE OXIDES

[75] Inventors: Percy Hayden; Richard W. Clayton, both of Middlesbrough, England

[73] Assignee: Imperial Chemical Industries Limited, London, England

[21] Appl. No.: 796,068

[22] Filed: May 12, 1977

[30] Foreign Application Priority Data

May 28, 1976 [GB] United Kingdom ............... 22286/76
Sep. 13, 1976 [GB] United Kingdom ............... 37832/76
Feb. 11, 1977 [GB] United Kingdom ................. 5710/77

[51] Int. Cl.² ........................ B01J 23/04; B01J 23/50
[52] U.S. Cl. ................................. 252/476; 260/348.34
[58] Field of Search ............................. 252/463, 476; 260/348.5 R, 348.34

[56] References Cited

U.S. PATENT DOCUMENTS

| 3,563,913 | 2/1971 | DeKrijger et al. | 252/477 R |
| 3,962,136 | 6/1976 | Nielsen et al. | 252/454 |
| 4,010,115 | 3/1977 | Nielsen et al. | 252/463 X |
| 4,012,425 | 3/1977 | Nielsen et al. | 260/348.5 R |
| 4,033,903 | 7/1977 | Maxwell | 252/476 |

Primary Examiner—W. J. Shine
Attorney, Agent, or Firm—Cushman, Darby & Cushman

[57] ABSTRACT

Catalysts for the oxidation of alkenes to alkylene oxides comprise silver on a support of 0.05 to 10m²/g surface area, a promoting amount of sodium and also potassium, rubidium and/or cesium.

8 Claims, No Drawings

CATALYSTS FOR THE PRODUCTION OF ALKYLENE OXIDES

This invention relates to the production of alkylene oxides and catalysts therefor.

The invention provides catalysts for the production of alkylene oxides for example ethylene and propylene oxides by oxidation of the corresponding olefine with oxygen which comprise silver supported on a porous heat resisting support which has a specific surface area in the range 0.05 to 10 m$^2$/g and preferably 0.01 to 5 m$^2$/g and more preferably 0.3 to 5 m$^2$/g as measured by the Brunauer Emmett and Teller method, the catalyst also comprising a promoting amount of sodium together with at least one other alkali metal selected from potassium, rubidium and cesium, in excess of any present in the support as impurities or cements. The said sodium and other alkali metal should preferably be extractable by contact with water.

The support is suitably a preformed support.

By "promoting" is meant that the activity or preferably selectivity of the catalyst is enhanced at any time in the life of the catalyst; the initial selectivity may for example thus be higher and/or it may be maintained for longer.

Silver may be introduced to a pre-formed porous heat resisting support as a suspension of silver or silver oxide in a liquid medium for example water or by impregnation of the support with a solution of a silver compound which can be reduced to silver metal if necessary by means of a reducing agent for example hydrogen. If necessary a heat treatment may be used to decompose the silver compound to silver. Suitably the impregnating solution contains a reducing agent which may be for example an anion, for example a formate, acetate, propionate, lactate, oxalate or tartarate ion, of a silver compound in the solution. The reducing agent may be for example an aldehyde, for example formaldehyde or acetaldehyde or an alcohol preferably having 1 to 4 carbon atoms for example methanol or ethanol.

The solution may be a solution in water and/or an organic solvent, for example an aliphatic alcohol preferably having 1 to 4 carbon atoms, a polyhydric alcohol for example ethylene glycol or glycerol, a ketone for example acetone, an ether for example dioxan or tetrahydrofuran, a carboxylic acid for example acetic acid or molten lactic acid which is preferably used in the presence of water, or an ester for example ethyl acetate or a nitrogen containing base for example pyridine or formamide. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution, for example it may be pyridine, acetonitrile, an amine, especially a primary or secondary amine having 1-6 carbon atoms, or preferably ammonia. Other suitable nitrogen-containing bases include acrylonitrile, hydroxylamine and alkanolamines for example ethanolamine, alkylene diamines having from 2-4 carbon atoms or amides for example formamide or dimethyl formamide. The nitrogen-containing bases may be used alone or in admixture, mixtures of ammonia and a second nitrogen containing base being preferred. Suitably the nitrogen containing base or bases are used together with water.

Alternatively the solution may be a neutral or acid solution for example it may be a solution of a silver carboxylate especially a formate, acetate, propionate, oxalate, citrate, tartarate or preferably lactate or for example a solution of silver nitrate.

The solutions preferably contain 3-50% of silver by weight.

Impregnation may be carried out in a single stage or if desired may be repeated one or more times. By this means higher silver contents of the catalyst may be achieved.

The silver compound may generally be reduced to silver by heating in the range 100° to 350° C., for example for a period of 15 mins. to 4 hours.

The catalyst support preferably has an apparent porosity as measured by the mercury absorption method of at least 20%, for example 30–80% preferably 30–65% and more preferably 40–60% and mean pore diameters of 0.1 to 20 microns preferably 0.3 to 4 microns as measured by the mercury porosimetry method. The pore size distribution of the support may be bimodal, in which case the smaller pores preferably account for at least 70% of the total pore volume and have a mean pore diameter preferably in the range of 0.1 and preferably 0.3 to 4 microns, and the larger pores preferably have a mean pore diameter in the range 25 to 500 microns.

Most of the silver content of the catalyst is preferably present in the form of discrete particles adhering to the support having equivalent diameters of less than 10,000 Å preferably in the range 20–10,000 Å and more preferably 40–8,000 Å. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver may be present as silver and/or silver oxide and is thought to be present normally as silver particles having a surface layer of silver oxide. The dimensions of the silver particles may be determined by scanning electron microscopy.

The support may be an alumina, silicon carbide, silica, zirconia or silica/alumina support, but it is preferably composed of an aggregate of alpha-alumina particles which may be fused together or cemented together with, for example, silica or baryta.

The catalyst preferably comprises 3 to 50% and more preferably 3 to 30% for example 6 to 28% by weight of silver.

The preferred levels of sodium, potassium, rubidium and cesium in excess of any present in the preformed support as impurities or cements are related to the surface area of the support. In general the preferred level expressed as a percentage by weight of the catalyst is $K'\sqrt{S}$ in respect of sodium where $K'$ is a constant in the range 0.01 to 3 and preferably 0.03 to 1 and more preferably 0.06 to 0.6, and S is the surface area of the support in square meters per gram. The preferred level of potassium expressed as a percentage by weight of the catalyst is $K''S$ where $K''$ is a constant preferably in the range 0.001 to 0.6, more preferably 0.003 to 0.1, and S is as previously defined. The preferred level for rubidium or cesium individually expressed as a percentage by weight of the catalyst is $K'''S^2$ where $K'''$ is a constant in the range 0.001 to 1, more preferably 0.003 to 0.6 for example in the range 0.03 to 0.3 and S is as before defined. The form in which the sodium, potassium, rubidium and cesium is present is determined by the conditions under which an oxidation of an olefine to an olefine oxide is carried out using the catalyst. Providing that catalyst poisons are absent it is believed that the form in which the alkali metal is introduced is irrelevant. It is preferred that bromine, iodine and sulphur are substantially absent and that the sodium, potassium, rubidium and/or cesium present should be in a form which is extractable by contacting the catalyst with water.

The promoters may be introduced to the support before during or after impregnation with a solution of the silver compound. The promoters are suitably introduced as solutions of compounds of the promoting elements, which solutions may be in water and/or organic solvents. They may comprise solvents, reducing agents and/or complexing agents as previously described. If it is desired to impregnate a catalyst which has already been used in the oxidation of an alkene to an alkylene oxide and has lost performance, this may be carried out also, whether or not the catalyst already contains one or more promoters. It may also be possible to regenerate a catalyst according to the invention which has deteriorated in performance in use by contacting it with water and/or an organic solvent as previously described. The catalyst after treatment as aforesaid is heated to a temperature at which promotion becomes effective, normally in the range 100° to 350° C.; such heating may serve to decompose the silver compound if present also.

The invention also provides processes for the production of alkylene oxides for example ethylene and propylene oxides by the oxidation of the corresponding olefine with oxygen using a catalyst as aforesaid.

Partial pressures of ethylene or propylene in such processes may be in the ranges 0.1–30 and preferably 1 to 30 bars. The total pressure may be in the range of from 1 to 100 and preferably 3–100 bars absolute. The molar ratio of oxygen to ethylene or propylene may be in the range 0.05 to 100. The partial pressure of oxygen may be in the range 0.01 and preferably 0.1 to 20 bars and preferably 1–10 bars. The oxygen may be supplied for example in the form of air or preferably as commercial oxygen. A diluent for example helium, nitrogen, argon and/or carbon dioxide and/or preferably methane may be present in proportions of 10–80% and preferably 40–70% by volume in total. It is necessary to operate using gas compositions which are outside the explosive limits.

The temperature is suitably in the range 200°–300° C. and preferably in the range 220°–290° C. Contact times should be sufficient to convert 0.5–70%, for example 2 to 20 and preferably 5–20% of the ethylene or propylene and unconverted ethylene or propylene is suitably recycled.

A reaction modifier is suitably present. Suitable reaction modifiers comprise chlorine and may be for example chlorinated alkenes having 1–6 carbon atoms for example methyl chloride or tertiary butyl chloride, di-chloromethane or chloroform, a chlorinated biphenyl or polyphenyl, a chlorinated benzene which may be for example mono chloro- or dichloro benzene, or especially ethylene dichloride. The concentration of the reaction modifier depends on its chemical nature for example in the case of ethylene dichloride 0.1 to 100 and preferably 0.5–25 parts per million are normally present and in the case of vinyl chloride 0.1 to 200 and preferably 0.5 to 40 parts per million are suitably present.

It is preferred that the reaction modifier should be a chlorine containing reaction modifier which does not readily dehydrochlorinate under the reaction conditions and contains a carbon-chlorine bond for example methyl chloride, dichloromethane, 1,1-dichloroethylene and 1,2-dichloroethylene, or espcially vinyl chloride. Chlorinated aromatic compounds for example chlorobenzene, dichlorobenzenes and chlorinated toluenes are also suitable.

We have found that with appropriate concentrations of such reaction modifiers, especially vinyl chloride, attractive selectivities may be secured and that such selectivity is more stable than selectivity secured using for example dichloroethane which can undergo dehydrochlorination under reaction conditions.

EXAMPLE 1

Catalysts (1–22) for the oxidation of ethylene and propylene to ethylene oxide and propylene oxide were prepared as follows:

8 g of reagent grade silver acetate were dissolved into 8 ml. aqueous ammonia (S.G. 0.880) and the solution was filtered. Appropriate amounts of alkali metal salts were added to this solution followed by 1.2 ml ethanolamine. 6 ml of this solution was used to impregnate 30 g. of the support material. The support used was an alpha-alumina composite sold by Norton Co. under the trademark "ALUNDUM" which had previously been crushed and sieved to give particles with diameters in the range 0.42–1 mm. The surface area of the support material was 0.3 $m^2/g$, the mean pore diameter was 2.8 microns and the water porosity was 20%.

The support impregnated with the silver solution was heated in a forced draught oven for 4 hours, during which time the temperature was raised from 100° to 300° C. The procedure resulted in catalysts containing about 8% silver by weight. The promoter levels for the catalysts are given in Table 1 below. The sodium and potassium were added as the acetate while the rubidium and cesium promoters were added as the carbonates.

The catalysts were tested for catalytic activity for ethylene oxidation using the method described in Example 4. The results are displayed in Table 1.

EXAMPLE 2

Catalysts 23–33 for the oxidation of ethylene and propylene to ethylene oxide and propylene oxide were prepared as follows:

5.2 g. of reagent grade silver acetate were dissolved in the minimum amount of ammonia required to give complete dissolution. Appropriate amounts of the promoter compounds were added and the volume of the solution was increased to 6 ml. by the addition of water. This solution was used to impregnate 30 g. of the support material described in Example 1.

The impregnated support was then heated in a forced draught oven for 4 hours, during which time the temperature was raised from 100° to 300° C. The promoter levels are given in Table 2. Sodium was added as the acetate while rubidium and cesium were added as the carbonates. The catalysts were tested as in Example 4 and the results are given in Table 2.

EXAMPLE 3

Catalysts 34–37 for the oxidation of ethylene and propylene to ethylene oxide and propylene oxide were prepared as follows:

5.2 g of reagent grade silver acetate were dissolved in the minimum amount of ammonia required to give complete dissolution. The volume of the solution was increased to 6 ml. by the addition of water. This solution was raised to impregnate 30 g. of the support material described in Example 1. The impregnated support was then heated in a forced draught oven for 30 mins, during which time the temperature was raised from 70° to 275° C. to give catalyst A.

Catalyst 34 was prepared from catalyst A in the following way:

Sodium acetate and cesium carbonate were dissolved in 6 ml. water. Fresh unused catalyst A was impregnated with this solution and then heated at 300° C. for 1 hour. Catalyst 34 was tested as in Example 4.

Catalyst 35 was prepared from catalyst A in the following way. Sodium acetate and cesium carbonate were dissolved in the minimum quantity of water required for complete dissolution. The solution was then made up to 6 ml by the addition of methanol. This solution was used to impregnate fresh unused catalyst A. The resulting solid was then heated to 300° C. for 1 hour in a forced draught oven. Catalyst 35 was tested as in Example 4.

Catalyst 36 and 37 were prepared and tested by the method used for catalysts 34 and 35 except that catalyst A had been used for ethylene oxidation for a period of 10 weeks prior to the impregnation of the promoter solutions.

The composition and results obtained from catalysts 34–37 are shown in Table 3. The performance of catalyst A is also shown in Table 7 as a comparative example.

EXAMPLE 4

The catalysts prepared in Examples 1–3 were tested for catalytic activity in the following manner:

20 g. of catalyst was loaded into a stainless steel reactor (internal diameter 8 mm) contained in a thermostatically controlled fluidised sand bath. The catalyst was conditioned under increasingly severe reaction conditions until it reached a steady performance, with a process gas mixture containing 30% ethylene, 8% oxygen and 4–10 ppm ethylene dichloride at a pressure of 15 pounds per square inch. The selectivity and oxygen conversion was then measured at 240° C. with a gas hourly space velocity of 400 hr$^{-1}$. The total pressure of the process gas stream was then raised to 120 p.s.i. The catalyst performance was then allowed to stabilise and the selectivity and oxygen conversion measured at 240° C. with a GHSV of 4000 hr$^{-1}$.

The process gas pressure was then raised 240 p.s.i.a. The catalyst performance was then allowed to stabilise and the relatively and oxygen conversion measured at 240° C. with a GHSV of 4000 hr$^{-1}$.

EXAMPLE 5

Catalysts 38–48 were prepared for the oxidation of ethylene and propylene to ethylene oxide and propylene oxide were prepared as follows:

8.9 g. of silver oxalate were dissolved in 7 ml. of a solution of 50% 1,2-diaminoethane in water. The resulting solution was made up to 8 ml by the addition of ethanolamine. Appropriate amounts of sodium acetate, potassium acetate, rubidium carbonate and/or cesium carbonate were added to this solution which was then used to impregnate 20 g. of the support material. The support used was a porous alpha-alumina in the form of cylindrical pellets 3 mm diameter and 3 mm long. The surface area was 2.2 m$^2$g$^{-1}$, the mean pore diameter was 1 micron and the pore volume was 0.6 ml g$^{-1}$.

The impregnated support was heated at 290° C. for a period of 3 hours in a forced draught air oven. This procedure resulted in catalysts containing about 24% silver by weight. The levels of alkali metals added to the catalyst are given in Table 4. The catalysts were tested for catalytic activity using the method described in Example 7 and the results of these tests are given in Table 4.

EXAMPLE 6

Catalysts 49–52 were prepared as described in Example 5 except that 3 g. of silver oxalate were used in the preparation rather than 8.9 g. This results in catalysts containing about 8% by weight of silver. The levels of sodium and rubidium present in the catalyst are given in Table 4. The catalysts were tested for activity by the method described in Example 7. The results of these tests are also given in Table 4.

EXAMPLE 7

The catalysts prepared in Examples 5 and 6 were tested for activity in the following way:

5 g. of catalyst were loaded into a stainless steel reactor (internal diameter 8 mm). The catalyst was subjected to increasingly severe reaction conditions and, once the catalytic acitivty and selectivity had stabilised, the catalyst selectivity and oxygen conversion were measured using a process gas stream containing 30% ethylene, 8% oxygen, and 10 ppm vinyl chloride. The process gas pressure was 15 p.s.i.a., the gas hourly space velocity was 1,600 hr$^{-1}$ and the reactor temperature was maintained at 240° C. The process gas pressure was then raised to 240 p.s.i.a. and the selectivity and oxygen conversion were measured after the catalyst performance had stabilised. The gas hourly space velocity was 12,000 hr$^{-1}$ and the reactor temperature was 240° C. The results of the catalyst tests are shown in Table 4.

EXAMPLE 8

Several of the catalysts (Nos. 7, 10, 13, 21, 22) prepared in Example 1 were tested for catalytic activity for the oxidation of propylene to propylene oxide by the following method.

6 g of catalyst were loaded into a stainless steel reactor (internal diameter 4 mm). A process gas stream containing 30% ethylene, 8% oxygen, 10–20 ppm ethylene dichloride and 62% nitrogen at 15 p.s.i.a. total pressure was passed over the catalyst at 240° C. Once the catalyst performance had stabilised with the ethylene containing stream, the reactor was flushed out with a stream of pure nitrogen and a process gas stream containing 30% propylene, 8% oxygen and 10–20 ppm ethylene dichloride was introduced. The selectivity and oxygen conversion for the catalytic oxidation of propylene to propylene oxide was then measured at a reactor temperature of 240° C., a gas hourly space velocity of 200 hr$^{-1}$ and a process gas pressure of 15 p.s.i.a. The results of these catalyst tests are given in Table 5.

EXAMPLE 9

A catalyst for the oxidation of ethylene and propylene to ethylene oxide and propylene oxide was prepared as follows:

55.5 g of reagent grade silver acetate was dissolved in the minimum amount of ammonia required to give complete dissolution. Appropriate amounts of sodium acetate and rubidium carbonate were added and the volume of the solution was increased to 64 ml by the addition of water. This solution was used to impregnate 320 g. of support material. The support material used was an alpha-alumina composite sold by Norton Co. under the trade-mark "ALUNDUM" which had previously been crushed and sieved to give particles with diameters in the range 0.42–1 mm. The surface area of the support material was 0.3 m$^2$g$^{-1}$, the mean pore diameter was 2.8 microns and the water porosity was 20%.

The impregnated support was then heated in a forced draught oven for 4 hours, during which time the temperature was increased from 100° C. to 300° C. The final catalyst contained 8% by weight silver, 0.1% by weight sodium and 0.01% by weight rubidium.

EXAMPLE 10

The catalyst prrepared in Example 9 was tested for catalytic acitivity in the following manner:

A 20 g. sample of catalyst was loaded into a stainless steel reactor (internal diameter 8 mm) contained in a thermostatically controlled fluidised sand bath. The catalyst was subjected to increasingly severe reaction conditions until the process gas mixture contained 30% ethylene, 8% oxygen and 10 ppm ethylene dichloride at a pressure of 120 pounds per square inch. The selectivity and oxygen conversion was then measured at 240° C. with a gas hourly space velocity of 4000 hr$^{-1}$ (calculated at NTP) over a period of one month. The results of this catalyst test are shown in Table 1.

EXAMPLE 11

Other 20 g samples of the catalyst prepared in Example 1 were tested as in Example 10 except that different concentrations of ethylene dichloride were present in the process gas stream. Further samples were tested as in Example 10 with vinyl chloride present in the gas stream rather than ethylene dichloride. The results of these tests are shown in Table 6 together with the concentration and type of moderator used.

EXAMPLE 12

Catalysts (A–F) which are not included within the scope of the invention were prepared as comparative examples. Catalyst A was prepared by the method described in Example 3. This catalyst had no alkali metal promoters added to the silver solution. The promoted catalysts (B–F) were prepared by the method described in Example 1. The catalysts (A–F) were all tested for catalytic activity towards ethylene oxidation using the method described in Example 4. The promoter levels and the results of the catalyst tests are given in Table 7.

Catalysts (A, D and E) were also tested for catalytic activity for propylene oxidation using the method described in Example 8. The results of these tests are shown in Table 5.

In these examples the initials GHSV mean hourly space velocity and psia means pounds per square inch absolute.

TABLE 1

| Catalyst No. | Promoter levels (wt %) | | | | Selctivity at 15 p.s.i.a. % | Oxygen conversion at 15 psia % | Selectivity at 120 p.s.i.a. (%) | Oxygen Conversion at 120 psia (%) | Selectivity at 240 p.s.i.a. (%) | Oxygen Conversion at 240 psia (%) |
|---|---|---|---|---|---|---|---|---|---|---|
| | Na | K | Rb | Cs | | | | | | |
| 1 | 0.10 | 0.001 | — | — | 90 | 17 | 89 | 11 | 85 | 15 |
| 2 | 0.10 | 0.002 | — | — | 91 | 13 | 89 | 7 | 86 | 10 |
| 3 | 0.10 | 0.003 | — | — | 92 | 17 | 90 | 10 | 88 | 15 |
| 4 | 0.10 | 0.01 | — | — | 90 | 10 | 88 | 10 | 85 | 12 |
| 5 | 0.10 | 0.03 | — | — | 87 | 14 | 86 | 17 | 85 | 9 |
| 6 | 0.10 | — | 0.001 | — | 94 | 13 | 91 | 7 | 86 | 14 |
| 7 | 0.10 | — | 0.003 | — | 94 | 12 | 90 | 6 | 84 | 12 |
| 8 | 0.10 | — | 0.004 | — | 93 | 9 | 90 | 9 | 87 | 11 |
| 9 | 0.10 | — | 0.006 | — | 94 | 9 | 91 | 5 | 87 | 9 |
| 10 | 0.10 | — | 0.010 | — | 94 | 15 | 92 | 8 | 90 | 11 |
| 11 | 0.10 | — | 0.013 | — | 95 | 10 | 91 | 7 | 89 | 13 |
| 12 | 0.10 | — | 0.020 | — | 88 | 4 | 92 | 3 | 90 | 5 |
| 13 | 0.10 | — | 0.030 | — | 92 | 6 | 89 | 3 | 86 | 5 |
| 14 | 0.10 | — | 0.10 | — | 91 | 4 | 90 | 4 | 86 | 8 |
| 15 | 0.10 | — | — | 0.001 | 92 | 13 | 90 | 10 | 84 | 11 |
| 16 | 0.10 | — | — | 0.003 | 93 | 14 | 91 | 8 | 87 | 13 |
| 17 | 0.10 | — | — | 0.01 | 95 | 15 | 92 | 14 | 91 | 10 |
| 18 | 0.10 | — | — | 0.03 | 90 | 10 | 88 | 8 | 85 | 6 |
| 19 | 0.03 | — | — | 0.003 | 90 | 17 | 86 | 9 | 83 | 14 |
| 20 | 0.10 | — | — | 0.003 | 93 | 15 | 90 | 8 | 87 | 13 |
| 21 | 0.30 | — | — | 0.003 | 92 | 13 | 89 | 10 | 86 | 17 |
| 22 | 0.80 | — | — | 0.003 | 92 | 10 | 90 | 7 | 87 | 10 |

TABLE 2

| Catalyst No. | Prometer levels (Wt. %) | | | | Selectivity at 15 psia (%) | Oxygen Conversion at 15 psia (%) | Selectivity at 120 psia (%) | Oxygen Conversion at 120 psia (%) | Selectivity at 240 psia (%) | Oxygen Conversion at 240 psia (%) |
|---|---|---|---|---|---|---|---|---|---|---|
| | Na | K | Rb | Cs | | | | | | |
| 23 | 0.10 | — | 0.009 | 0.001 | 95 | 19 | 94 | 9 | 91 | 14 |
| 24 | 0.10 | — | 0.007 | 0.003 | 93 | 9 | 91 | 7 | 90 | 10 |
| 25 | 0.10 | — | 0.003 | 0.007 | 95 | 22 | 93 | 9 | 91 | 8 |
| 26 | 0.10 | — | 0.001 | 0.009 | 95 | 20 | 92 | 10 | 91 | 15 |

TABLE 2-continued

| Catalyst No. | Promoter levels (Wt. %) | | | | Selectivity at 15 psia (%) | Oxygen Conversion at 15 psia (%) | Selectivity at 120 psia (%) | Oxygen Conversion at 120 psia (%) | Selectivity at 240 psia (%) | Oxygen Conversion at 240 psia (%) |
|---|---|---|---|---|---|---|---|---|---|---|
| | Na | K | Rb | Cs | | | | | | |
| 27 | 0.10 | — | 0.01 | — | 93 | 15 | 91 | 10 | 90 | 12 |
| 28 | 0.10 | — | — | 0.003 | 93 | 22 | 90 | 12 | 89 | 15 |
| 29 | 0.10 | — | — | 0.01 | 94 | 25 | 92 | 12 | 91 | 17 |
| 30 | 0.03 | — | 0.01 | — | 93 | 20 | 93 | 8 | 89 | 11 |
| 31 | 0.06 | — | 0.01 | — | 94 | 20 | 94 | 8 | 89 | 10 |
| 32 | 0.10 | — | 0.01 | — | 94 | 21 | 94 | 7 | 91 | 8 |
| 33 | 0.30 | — | 0.01 | — | 94 | 19 | 95 | 6 | 91 | 8 |

TABLE 3

| Catalyst No. | Promoter levels wt % | | | | Selectivity at 15 psia (%) | Oxygen Conversion at 15 psia (%) | Selectivity at 120 psia (%) | Oxygen Conversion at 120 psia (%) |
|---|---|---|---|---|---|---|---|---|
| | Na | K | Rb | Cs | | | | |
| 34 | 0.1 | — | — | 0.01 | 94 | 18 | 92 | 15 |
| 35 | 0.1 | — | — | 0.01 | 94 | 25 | 92 | 20 |
| 36 | 0.1 | — | — | 0.01 | 94 | 17 | 92 | 16 |
| 37 | 0.1 | — | — | 0.01 | 94 | 25 | 92 | 21 |

TABLE 4

| Catalyst No. | Promoter levels (wt %) | | | | Selectivity at 15 psia (%) | Oxygen Conversion at 15 psia (%) | Selectivity at 240 psia (%) | Oxygen Conversion at 240 psia (%) |
|---|---|---|---|---|---|---|---|---|
| | Na | K | Rb | Cs | | | | |
| 38 | 0.3 | — | — | 0.06 | 93 | 11 | 90 | 5 |
| 39 | 0.3 | — | — | 0.40 | 93 | 12 | 92 | 5 |
| 40 | 0.3 | — | 0.01 | — | 84 | 17 | 82 | 20 |
| 41 | 0.3 | — | 0.03 | — | 86 | 12 | 84 | 12 |
| 42 | 0.3 | — | 0.06 | — | 92 | 6 | 87 | 4 |
| 43 | 0.3 | — | 0.15 | — | 93 | 8 | 88 | 3 |
| 44 | 0.3 | — | 0.40 | — | 93 | 7 | 89 | 2 |
| 45 | 0.3 | — | 0.8 | — | 44 | 3 | 90 | 3 |
| 46 | 0.3 | — | 1.60 | — | 24 | 4 | 85 | 2 |
| 47 | 1.0 | — | 0.15 | — | 93 | 5 | 86 | 2 |
| 48 | 1.5 | — | 0.15 | — | 85 | 3 | 91 | 4 |
| 49 | 0.1 | — | 0.05 | — | 93 | 5 | 88 | 2 |
| 50 | 0.1 | — | 0.15 | — | 93 | 11 | 90 | 2 |
| 51 | 0.3 | — | 0.05 | — | 95 | 4 | 89 | 2 |
| 52 | 0.3 | — | 0.15 | — | 95 | 8 | 89 | 2 |

TABLE 5

| Catalyst No. | Promoter Levels (wt %) | | | | Selectivity (%) | Oxygen Conversion (%) |
|---|---|---|---|---|---|---|
| | Na | K | Rb | Cs | | |
| 7 | 0.1 | — | .003 | — | 51 | 8 |
| 10 | 0.1 | — | 0.01 | — | 48 | 11 |
| 13 | 0.1 | — | 0.03 | — | 52 | 9 |
| 21 | 0.1 | — | — | 0.01 | 41 | 9 |
| 22 | 0.1 | — | — | 0.03 | 42 | 13 |
| COMPARATIVE EXAMPLES | | | | | | |
| A | — | — | — | — | 20 | 3 |
| D | — | — | 0.03 | — | 6 | 9 |
| E | — | — | — | 0.01 | 17 | 9 |

TABLE 6

| REACTION MODERATOR | | TIME | | | | | |
|---|---|---|---|---|---|---|---|
| Type | Level (ppm) | 2 days | | 7 days | | 20 days | |
| | | S (%) | C (%) | S (%) | C (%) | S (%) | C (%) |
| Ethylene dichloride | 10 | 93 | 13 | 87 | 7 | — | — |
| " | 20 | 93 | 10 | 91 | 5 | — | — |
| " | 30 | 94 | 4 | 93 | 4 | 91 | 4 |
| " | 50 | 92 | 2 | 92 | 2 | 92 | 2 |
| Vinyl chloride | 10 | 94 | 10 | 89 | 4 | — | — |
| " | 20 | 92 | 7 | 87 | 7 | — | — |
| " | 30 | 93 | 6 | 94 | 6 | 90 | 3 |
| " | 50 | 93 | 6 | 93 | 6 | 93 | 6 |
| " | 100 | 91 | 3 | 91 | 3 | 91 | 3 |

S—Selectivity i.e. moles Ethylene Oxide produced per mole Ethylene consumed.
C—Oxygen conversion.

TABLE 7
COMPARATIVE EXAMPLES

| Catalyst No. | Promoter levels (wt %) | | | | Selectivity at 15 psia (%) | Oxygen Conversion at 15 psia (%) | Selectivity at 120 psia (%) | Oxygen Conversion at 120 psia (%) |
|---|---|---|---|---|---|---|---|---|
| | Na | K | Rb | Cs | | | | |
| A | — | — | — | — | 81 | 20 | 79 | 18 |
| B | 0.1 | — | — | — | 90 | 16 | 82 | 7 |
| C | — | 0.01 | — | — | 84 | 18 | — | — |
| D | — | — | 0.03 | — | 78 | 3 | — | — |
| E | — | — | — | 0.01 | 80 | 28 | — | — |
| F | — | — | 0.01 | 0.01 | 34 | 11 | — | — |

We claim:

1. A catalyst for the production of alkylene oxides by oxidation of the corresponding olefin with oxygen which comprises silver supported on a porous heat resisting support which has a specific surface area in the range 0.05 to 10 sq. meters per gram as measured by the Brunauer, Emmett and Teller method, the catalyst also comprising a promoting amount of sodium and at least one other alkali metal selected from potassium, rubidium and cesium in excess of any present in the support as impurities or cements.

2. A catalyst as claimed in claim 1 in which the catalyst support has an apparent porosity as measured by the mercury absorption method of 30–80% and a mean pore diameter of 0.1 to 20 microns as measured by the mercury porosimetry method.

3. A catalyst as claimed in claim 1 in which the pore size distribution of the support is bimodal and in which the smaller pores account for at least 70% of the total pore volume and have a mean pore diameter in the range 0.1 to 20 microns, the larger pores having a mean pore diameter in the range 25 to 500 microns.

4. A catalyst as claimed in claim 1 in which at least 80% of the silver content of the catalyst is present in the form of discrete particles having equivalent diameters in the range 40 to 8,000 Å, which adhere to the support, the quantity of silver being judged in terms of the number of particles falling in the said range.

5. A catalyst as claimed in claim 1 in which the sodium content is $K'\sqrt{S}$, the potassium content is $K''S$, the rubidium content is $K'''S^2$ or the cesium content is $K'''S^2$, the alkali metal content being expressed as percentage of the alkali metal by weight based on the catalyst, $K'$ being a constant in the range 0.01 to 3, $K''$ being a constant in the range 0.001 to 0.6 and $K'''$ being a constant in the range 0.001 to 1 and S is the surface area of the catalyst in square meters per gram.

6. A process of producing a catalyst as claimed in claim 1 which comprises the steps of impregnating the support with a solution of a silver compound, reducing the silver compound to silver metal by heating at a temperature of 100° to 350° C. and introducing a promoting element as a solution a compound of the promoting element.

7. A process as claimed in claim 6 in which the solution comprises ammonia.

8. A process as claimed in claim 6 in which the alkali metals are introduced to the support by impregnation with an aqueous solution of a compound of the promoting element.